(12) United States Patent
Uckun et al.

(10) Patent No.: US 6,878,388 B1
(45) Date of Patent: Apr. 12, 2005

(54) VANADIUM COMPOUNDS FOR TREATING PROLIFERATIVE CELL DISORDERS

(75) Inventors: Fatih M Uckun, White Bear Lake, MN (US); Rama Krishna Narla, Shoreview, MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 09/713,379

(22) Filed: Nov. 15, 2000

(51) Int. Cl.$^7$ ...................... A61K 31/28; A61K 31/555; A61K 33/24; A61P 17/06; A61P 35/00
(52) U.S. Cl. ....................... 424/646; 514/184; 514/185; 514/186; 514/187; 514/188; 514/290; 514/291; 514/292; 514/492; 514/822; 514/824; 514/863; 514/883
(58) Field of Search ................................ 514/184–188, 514/290–292, 492, 822, 824, 863, 883, 287, 908; 424/646

(56) References Cited

U.S. PATENT DOCUMENTS

| 4,559,157 A | 12/1985 | Smith et al. ................. 424/401 |
| 4,608,392 A | 8/1986 | Jacquet et al. .............. 514/772 |
| 4,820,508 A | 4/1989 | Wortzman .................... 424/59 |
| 4,938,949 A | 7/1990 | Borch et al. ................. 514/476 |
| 4,992,478 A | 2/1991 | Geria ........................ 514/782 |
| 6,432,941 B1 | 8/2002 | Uckun et al. ............... 514/185 |

FOREIGN PATENT DOCUMENTS

| WO | 98/49173 | * 11/1998 |
| WO | WO 99/36063 | 7/1999 |
| WO | WO 00/27389 | 5/2000 |
| WO | WO 00/35930 | 6/2000 |

OTHER PUBLICATIONS

Medline Abstract, accession No. 2000239529, abstracting Clinical Cancer Research, vol. 6(4), pp. 1546–1556 (Apr. 2000).*
Albini, A. et al., "Chemotaxis of 3T3 and SV3T3 Cells to Fibronectin Is Mediated through the Cell–Attachment Site in Fibronectin and a Fibronectin Cell Surface Receptor", *The Journal of Cell Biology*, vol. 105, No. 4, pp. 1867–1872 (Oct. 1987).
Brown, L. et al., "Vascular Stroma Formation in Carcinomain Situ, Invasive Carcinoma, and Metastatic Carcinoma of the Breast", *Clinical Cancer Research*, vol. 5, No. 5, pp. 1041–1056 (May 1999).
Carbonetto, S. et al., "In Vitro studies on the control of nerve fiber growth by the extracellular matrix of the nervous system", *J. Physiol., Paris*, vol. 82, pp. 258–270 (1987).
Carbonetto, S., "Facilitatory and inhibitory effects of glial cells and extracellular matrix in axonal regeneration" *Current Opinion in Neurobiology*, vol. 1, pp. 407–413 (1991).
Chintala, S. et al., "Invasion of Human Glioma: Role of Extracellular Matrix Proteins",*Frontiers in Bioscience*, vol. 1, pp. 324–329 (Nov. 1, 1996).

Djordjevic, C. et al., "Antitumor Activity and Toxicity of Peroxo Heteroligand Vanadates(V) in Relation to Biochemistry of Vanadium", *Journal of Inorganic Biochemistry*, vol. 25, pp. 51–55 (Sep. 1985).
Djordjevic, C., "Antitumor Activity of Vanadium Compounds", *Department of Chemistry, The College of William and Mary*, Ch. 18, pp. 595–616 (1995).
Dubyak, G., et al. "The Insulin–mimetic Effects of Vanadate in Isolated Rat Adipocytes", *The Journal of Biological Chemistry* vol. 255, No. 11, pp. 5306–5312 (Jun. 10, 1980).
Faure, R. et al., "Arrest at the G2/M Transition of the Cell Cycle by Protein–Tyrosine Phosphatase Inhibition: Studies on a Neuronal and a Glial Cell Line",*Journal of Cellular Biochemistry*, vol. 59, No. 3, pp. 389–401 (Nov. 1995).
Friedman, H. et al., "Activity of Temozolomide in the Treatment of Central Nervous System Tumor Xenografts", *Cancer Research*, vol. 55, No. 13, pp. 2853–2857 (Jul. 1, 1995).
Ghosh, S. et al., "Structure–based design of potent inhibitors of EGF–receptor tyrosine kinase as anti–cancer agents", *Anti–Cancer Drug Design*, vol. 14, No. 5, pp. 403–410 (Oct. 1999).
Giese, A. et al., "Substrates for Astrocytoma Invasion", *Neurosurgery*, vol. 37, No. 2, pp. 294–302 (Aug. 1995).
Giese, A. et al., "Migration of Human Glioma Cells on Myelin", *Neurosurgery*, vol. 38, No. 4, pp. 755–764 (Apr. 1996).
Giese, A. et al., "Glioma Invasion in the Central Nervous System", *Neurosurgery*, vol. 39, No. 2, pp. 235–252 (Aug. 1996).
Heylinger, C. et al., "Effect of Vanadate on Elevated Blood Glucose and Depressed Cardiac Performance of Diabetic Rats", *Science*, vol. 227, pp. 1474–1477 (Mar. 1985).
Huang, H.–J. et al., "The Enchanced Tumorigenic Activity of a Mutant Epidermal Growth Factor Receptor Common in Human Cancers is Mediated by Threshold Levels of Constitutive Tyrosine Phosphorylation and Unattenuated Signaling", *The Journal of Biological Chemistry*, vol. 272, No. 5, pp. 2927–2935 (Jan. 31, 1997).
Kopf–Maier, P. et al., "Tumor Inhibition by Metallocenes: Activity against Leukemias and Detection of the Systemic Effect", *European Journal of Cancer*, vol. 17, No. 6, pp. 665–669, (Jun. 1981).

(Continued)

Primary Examiner—John Pak
(74) Attorney, Agent, or Firm—Merchant & Gould P.C.

(57) ABSTRACT

Vanadium compounds useful to prevent and/or inhibit adhesion, migration, and invasion of proliferative cells into surrounding tissue.

34 Claims, 2 Drawing Sheets

OTHER PUBLICATIONS

Kopf–Maier, P. et al., "Cytokinetic Behavior of Ehrlich Ascites Tumor After in vivo Treatment with cis–Diamminedichloroplatinum(II) and Metallocene Dichlorides", *Journal of Cancer Research and Clinical Oncology*, vol. 201, pp. 21–30 (1981).

Kopf–Maier, P. et al., "Induction of Cell Arrest at $G_1S$ and in $G_2$ After Treatment of Ehrlich Ascites Tumor Cells with Metallocene Dichlorides and cis–Platinum in vitro", *Journal of Cancer Research and Clinical Oncology*, vol. 106, No. 1, pp. 44–52 (1983).

Merzak, A. et al., "Adhesion of Human Glioma Cell Lines to Fibronectin, Laminin, Vitronectinand Collagen I Is Modulated by Gangliosides in vitro", *Cell Adhesion & Communication*, vol. 3, pp. 27–43 (1995).

Morinville, A. et al., "From Vanadis to Atropos: vanadium compounds as pharmacological tools in cell death signalling", *Trends in Pharmacological Sciences*, vol. 19, pp. 452–460 (Nov. 1998).

Nagano, N. et al., "Invasion of experimental rat brain tumor: early morphological changes following microinjection of C6 glioma cells", *Acta Neuropathol*, vol. 86, No. 1, pp. 117–125 (1993).

Narla, R. et al., 4–(3'–Bromo–4"hydroxylphenyl)–amino–6, 7dimethoxyquinazoline: A Novel Quinazoline Derivative with potent Cytotoxic Activity against Human Glioblastoma Cells, *Clinical Cancer Research*, vol. 4, No. 6, pp. 1405–1414 (Jun. 1998).

Pilkington, G.J., "The role of the extracellular matrix in neoplastic glial invasion of the nervous system" *Brazilian Journal of Medical and Biological Research*, vol. 29, pp. 1159–1172 (Sep. 1996).

Pilkington, G.J., "In Vitro and in Vivo Models for the Study of Brain Tumour Invasion", *Anticancer Researach*, vol. 17, No. 6B, pp. 4107–4110 (Nov.–Dec. 1997).

Rooprai, H. et al., "The role of Integrin Receptors in Aspects of Glioma Invasion In Vitro", *Int. J. Devl. Neuroscience*, vol. 17, Nos. 5–6, pp. 613–623 (1999).

Rutka, J. et al., "The extracellular matrix of the central and peripheral nervous systems: structure and function", *J. Neurosurg*, vol. 69, pp. 155–170 (Aug. 1988).

Sakurai, H. et al., "Mechanism for a New Antitumor Vanadium Complex: Hydroxyl Radical–Dependent DNA Cleavage by 1, 10–Phenanthroline–Vanadyl Complex in the Presence of Hydrogen Peroxide", *Biochemical and Biophysical Research Communications*, vol. 206, No. 1, pp. 133–137 (Jan. 5, 1995).

Schieven, G. et al., "Lineage–specific Induction of B Cell Apoptosis and Altered Signal Transduction by the Phosphotyrosine Phosphatase Inhibitor Bis(maltolato)oxovanadium (IV)", *The Journal of Biological Chemistry*, vol. 270, No. 35, pp. 20824–20831 (Sep. 1, 1995).

Schiffer, D. et al., "The vascular response to tumor infiltration in malignant gliomas–morphometric and reconstruction study", *Acta Neuropathol*, vol. 77, No. 4, pp. 369–378 (1989).

Schwartz, M., "Role of Trace Elements in Cancer", *Cancer Researach*, vol. 35, pp. 3481–3487 (Nov. 1975).

Selbin, J., "The Chemistry of Oxovanadium (IV)", *Chemical Reviews*, vol. 65, No. 2, pp. 153–175 (Mar. 25, 1965).

Shechter, Y. et al., "Insulin–like stimulation of glucose oxidation in rat adipocytes by vanadyl (IV) ions", *Nature*, vol. 284, pp. 556–558, (Apr. 10, 1980).

Tolman, E. et al., "Effects of Vanadium on Glucose Metabolism in Vitro", *Life Sciences*, vol. 25, No. 13, pp. 1159–1164 (Sep. 24, 1979).

Venstrom, K. et al., "Extracellular Matrix 2: Role of extracellular matrix molecules and their receptors in the nervous system", *The FASEB Journal*, vol. 7, pp. 996–1003 (Aug. 1993).

\* cited by examiner

VANADIUM COMPOUNDS FOR TREATING PROLIFERATIVE CELL DISORDERS

BACKGROUND OF THE INVENTION

A hallmark of cancer, i.e., a malignant tumor, is its ability to infiltrate, invade and metastasize to a distant site. It is this ability to develop at a secondary site, discontinuous with the original or primary site, that often results in an extremely poor prognosis and outcome for most cancer patients. It is well known that dissemination of a cancer to secondary sites strongly prejudices the possibility that the patient will be cured of the disease.

Approximately 30% of newly diagnosed patients having a solid tumor will present with some type of metastatic disease, and another 20% will have occult metastases at the time of diagnosis. Currently, radiotherapy and chemotherapy are two important methods used in the treatment of metastatic cancer. Considerable efforts are underway to develop new chemotherapeutic agents to limit and prevent dissemination of cancer to secondary sites.

The use of vanadium compounds and vanadium salts for clinical applications received renewed interest in the late 1970s and early 1980s due to the discovery that vanadate(V) solutions produced insulin-like effects in rat diaphragms and isolated adipocytes in vitro (Tolman et al., *Life Sci.* 25:1159–1164, 1979; Dubyak et al., *J Biol Chem,* 255: 5306–5312, 1980; Shechter et al., *Nature,* 284: 556–558, 1980). Subsequently, the administration of vanadate solutions to diabetic rats was shown to lower blood glucose levels (Heyliger et al., *Science,* 277: 1474–1477, 1985). Despite a long history of vanadium compounds being used in the treatment of human diseases, however, only a small number of organometallic compounds containing vanadium have been tested for antitumor activity (Morinville et al., *Trends Pharmacol. Sci.* 19: 452–460, 1998; Kopf-Maier, P, *Eur. J Clin Pharmacol,* 47: 1–16, 1994; Schwartz M. K., *Cancer Res.,* 35: 3481–3487, 1975; Djordjevic, C., *J Inorg Biochem,* 25: 51–55, 1985; Djordjevic C., In: H. Sigel and A. Sigel (eds.), *Metal ions in biological systems,* 31: 595–616, New York: Marcel Dekker, 1995; Schieven et al., *J Biol Chem,* 270: 20824–20831, 1995; Fature et al., *J Cell Biochem,* 59: 389–401, 1995); a few of these were shown in the late 1970s and 1980s to possess anticancer activity in vitro as well as in vivo (Kopf-Maier, P, *Eur J Clin Pharmacol,* 47: 1–16, 1994; Djordjevic C., In: H. Sigel and A. Sigel (eds.), *Metal ions in biological systems,* 31: 595–616, New York: Marcel Dekker, 1995; Kopf-Maier et al, *J Cancer Res Clin Oncol,* 102: 21–30, 1981; Kopt-Maier et al., *Eur J Cancer,* 17: 665–669, 1981; Kopf-Maier et al., *J Cancer Res Clin Oncol,* 106: 44–52, 1983.

Further, Sakurai, et al., *BBRC,* Vol. 206, p. 133 (1995) discloses an oxovanadium compound ([VO(Phen)($H_2O$)$_2$](SO$_4$)) that is active against pharyngonasal cancer as determined by a single assay, and Holmes, Ph.D. Thesis, LSU 1961, and Selbin, *Chem. Rev.,* Vol. 65, p. 155, 1965, disclose oxovanadium compounds [VO(SO$_4$)(Phen)$_2$] and [VO(ClO$_4$)Bpy)$_2$], but do not disclose biological data for the compounds.

Vanadocene dichloride (VDC) has been shown to arrest tumor cell growth (Kopf-Maier, et al., *J. Cancer Res. Clin. Onccol.,* 106: 44–52. 1983), and the oxovanadium compound, [VO(Phen)($H_2O$)$_2$](SO$_4$), has been shown to be an active pharyngonasal cancer as determined by a single assay (Sakurai, et al, *BBRC,* 206; 133, 1995). Vanadium compounds have also been shown to induce apoptosis in certain cancer cells (Uckun et al., WO 00/35930).

Against this backdrop the present invention has been developed.

SUMMARY OF THE INVENTION

The invention provides a method for treating or preventing metastatic cancer by contacting or administering an inhibitory amount of a vanadium compound. Exemplary compounds useful in the method of the invention are described, for example, in published PCT applications WO 99/36063; WO 00/27389; and WO 00/35930. Specific compounds useful in the method invention, as well as other compounds of the invention are described more fully below. A preferred compound for preventing metastatic cancer is bis(4,7-dimethyl-1,10-phenanthroline) sulfatooxovanadium (IV) [(VO(SO$_4$)(Me-Phen)$_2$].

The invention also provides a method for inhibiting or disrupting adhesion, invasion and migration of cancer cells into surrounding tissue, by contacting or administering to the cell a vanadium compound as described herein, in an amount sufficient to inhibit adhesion, invasion and migration into the surrounding tissue. The method invention is useful for the treatment of malignant type cancers, as well as in any other application where the inhibition of adhesion, invasion and migration of a cell into surrounding tissue is desired and useful.

BRIEF DESCRIPTION OF THE DRAWINGS

The invention may be more completely understood in consideration of the following detailed description of various embodiments of the invention in connection with the accompanying drawings, in which.

DETAILED DESCRIPTION OF THE PREFERRED EMBODIMENTS

Figures 1A, 1B:
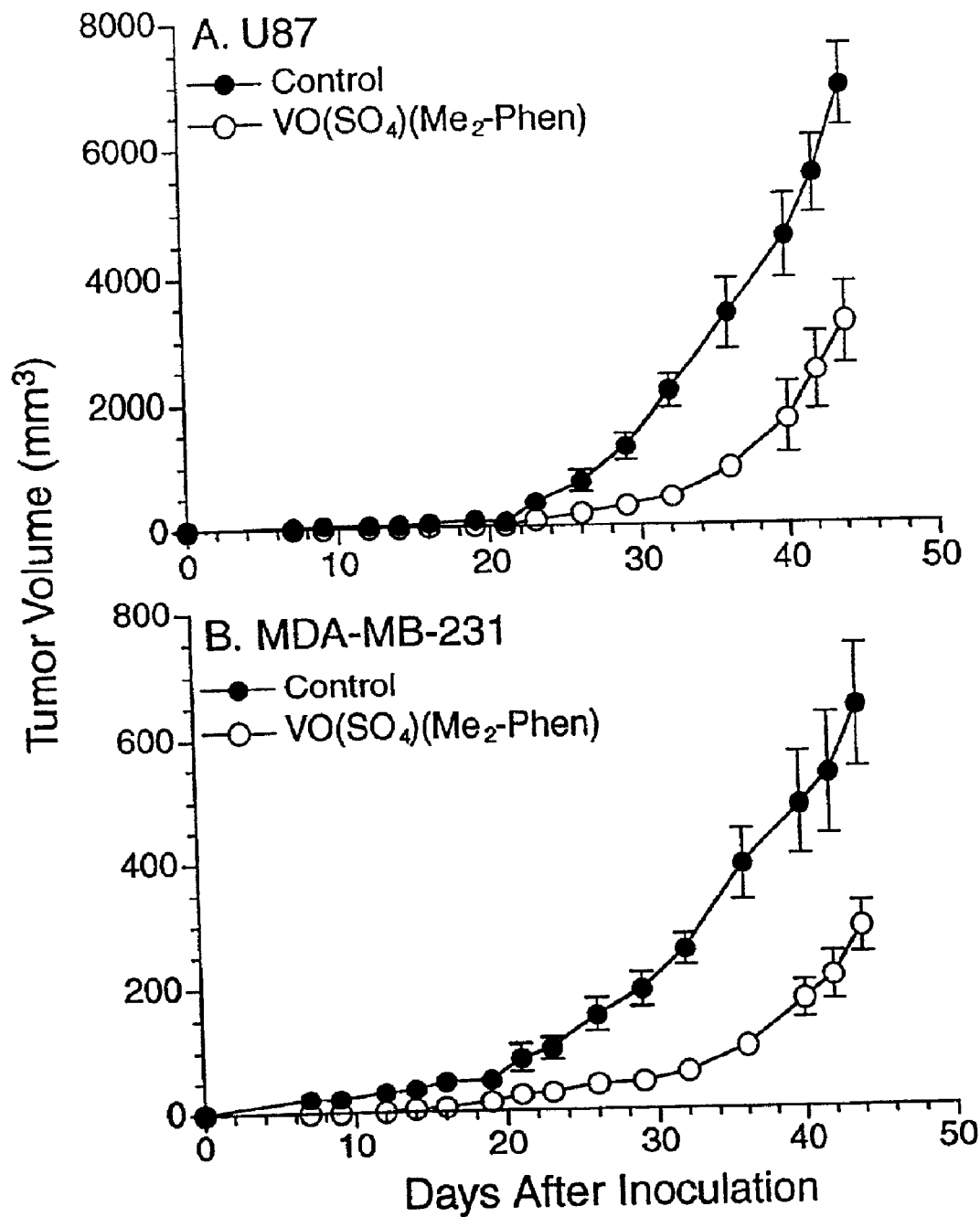
FIGS. 1A–1B illustrate the in vivo antitumor activity of the vanadium compound, [VO(SO$_4$)(Me$_2$-Phen)$_2$] against human glioblastoma and breast cancer in SCID mice. The effects of daily treatment with [VO(SO$_4$)(Me$_2$-Phen)$_2$] (10 mg/kg/day) or 5% DMSO in PBS (given five days per week for four weeks beginning the day after inoculation) on tumor growth and progression of glioblastoma (FIG. 1A) and breast cancer (FIG. 1B) are illustrated. Comparisons between groups were done using the log-rank test.

It has now been discovered that vanadium compounds such as the vanadocene and oxovanadium compounds disclosed herein, are effective inhibitors of metastatic cell adhesion, migration, and invasion. Accordingly, the method invention includes the use of these vanadium compounds to treat, prevent, and/or inhibit metastatic cancer. Compounds useful in the method invention are disclosed in the detailed description below, and include for example, bis(4,7-dimethyl-1,10-phenanthroline) sulfatooxovanadium (IV) [(VO(SO$_4$)(Me-Phen)$_2$], Exemplary compounds useful in the method of the invention are described, for example, in published PCT applications WO99/36063; WO 00/27389; and WO 00/35930. The present compounds are also shown to be potent inhibitors of cell adhesion, between the cell and extracellular matrix (ECM) proteins, further, the compounds inhibit invasion and migration of cancer cells into surrounding tissue.

Vanadium is a physiologically essential element that can be found in both anionic and cationic forms with oxidation states ranging from −3 to +5 (I–V). This versatility provides unique properties to vanadium complexes. In particular, the catonic form of vanadium complexes with oxidation state +4 (IV) have been shown to function as modulators of cellular redox potential, regulate enzymatic phosphorylation, and exert pleiotropic effects in multiple biological systems by catalyzing the generation of reactive oxygen species (ROS). Besides the ability of vanadium metal to assume various oxidation states, its coordination chemistry also plays a key role in its interactions with various biomolecules. In particular, it is shown in this disclosure that oxovanadium complexes, or derivatives thereof, induce apoptosis in tumor cells, and inhibit the adhesive, invasive and migratory properties of cancer cells.

Definitions

The following terms and phrases as used herein have the noted definitions, unless otherwise described:

"Halo" is fluoro, chloro, bromo, or iodo.

"Alkyl", "alkoxy", etc. denote both straight and branched hydrocarbon groups; but reference to an individual radical such as "propyl" embraces only the straight chain radical, a branched chain isomer such as "isopropyl" is specifically referenced.

"Organometallic compound" is an organic compound comprised of a metal attached directly to carbon (R-M).

"Coordination compound" is a compound formed by the union of a central metal atom or ion with ions or molecules called ligands or complexing agents.

"Ligand" or a "complexing agent" is a molecule, ion or atom that is attached to the central metal atom or ion of a coordination compound.

"Monodentate ligand" is a ligand having a single donor atom coordinated to the central metal atom or ion.

"Bidentate ligand" is a ligand having two donor atoms coordinated to the same central metal atom or ion.

"Vanadocene" is a compound having a central vanadium metal ion coordinated with at least two cyclopentadiene groups.

"Extracellular matrix" for purposes of the invention includes both basement membranes and intestitital connective tissue and corresponding proteins, glycoproteins, and proteoglycans.

"Surrounding tissue" means any site beyond where the migrating or invading cell originated, i.e., any distance from where the cell was created during cell division. The surrounding tissue as used herein includes ECM.

"Non-cancer proliferative disorder" includes such disorders as non-cancer proliferative disorders such as epithelial hyperplasia, polycyctemia, erythrocytemia, thrombocytemia, EBV transformed lymphoproliferative syndrome, dysplastic nevus syndrome, restenosis after angioplasty for coronary heart disease, mastocytosis, histiocytosis, psoriasis, polyps, and the like.

"Treating", as used herein includes preventative treatment.

It will be appreciated that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixture thereof, of a compound of the invention, which posses the useful properties described herein. Methods to prepare optically active forms are known, for example, by resolution of the racemic form by recrystallization techniques, by synthesis from optically-active starting materials, by chiral synthesis, or by chromatographic separation using a chiral stationary phase. Methods for determining anti-mitotic and anti-meiotic activity of a compound are known, for example, using the standard tests described herein, or other known tests.

Specific values listed below for radicals, substituents, and ranges, are for illustration only; they do not exclude other defined values or other values within defined ranges for the radicals and substituents.

For example, $(C_1-C_6)$ alkyl can be methyl, ethyl, propyl, isopropyl, butyl, iso-butyl, sec-butyl, pentyl, 3pentyl, or hexyl; $(C_1-C_3)$ alkyl can be methyl, ethyl or propyl; halo $(C_1-C_3)$ alkyl can be iodomethyl, bromomethyl, chloromethyl, fluoromethyl, trifluoromethyl, 2-chloroethyl, 2-fluoromethyl, 2,2,2-trifluorethyl, or pentafluoroethyl; $(C_1-C_3)$ alkoxy can be methoxy, ethoxy, or propoxy; and $(C_2-C_6)$alkanoyloxy can be acetoxy, propanoyloxy, butanoyloxy, isobutanoyloxy, pentanoyloxy, or hexanoyloxy.

The following glossary of vanadium compounds is provided to clarify terms used throughout the specification and provides a listing of exemplary vanadium compounds useful in the method invention:

Group A: Vanadocene dihalides

VDC Vanadocene dichloride $(Cp_2VCl_2)$

VMDC Bis(methyl cyclopentadienyl) vanadium dichloride $[(MeCp)_2VCl_2]$

VDB Vanadocene dibromide $(Cp_2VBr_2)$

VDI Vanadocene diiodide $(Cp_2VI_2)$

Group B: Vanadocene di-pseudohalides

VDA Vanadocene diazide $[Cp_2V(N_3)_2]$

VDCN Vanadocene dicyanide $(Cp_2V(CN)_2)$

VDOCN Vanadocene dioxycyanate $(Cp_2V(OCN)_2)$

VDSCN Vanadocene dithiocyanate $(Cp_2V(SCN)_2)$

VDSeCN Vanadocene diselenocyanate $(VCp_2(SeCN)_2)$

Group C: Vanadocene disubstituted derivatives

VDT Vanadocene ditriflate $(Cp_2V(O_3SCR_3)_2)$

VDCO Vanadocene monochloro oxycyanate $(Cp_2V(OCN)(Cl))$

VDFe Vanadocene monoacetonitrilo monochloro tetrachloro ferrate $(Cp_2VClNCCH_3)FeCl_4$ Group D: Chelated Vanadocene Complexes VDacac Vanadocene acetylacetonato monotriflate $(Cp_2V(CH_3COCH_2COCH_3)(O_3SCF_3)$ VDBPY Vanadocene bipyridino ditriflate $(CP_2V(C_{10}H_8N_2)(O_3SCF_3)_2)$ VDHfacac Vanadocene hexafluoro acetylacetonoato monotriflate $Cp_2V(CF_3COCH_2COCF_3)(O_3SCF_3))$ VDH Vanadocene acetohydroxamato monotriflate $(Cp_2V(CH_3CON(O)H)(O_3SCF_3)$ VDPH Vanadocene N-phenyl benzohydroxamato monotriflate $(CP_2V(C_6H_5CON(O)C_6H_5)(O_3SCF_3)$ Group E. Oxovanadium Compounds

[(VO(phen)]=(diaqua)(1,10-phenanthroline) oxovanadium (IV) sulfate;

[VO(phen)$_2$](aqua)bis(1,10-phenanthroline) oxovanadium (IV) sulfate;

[VO(Me$_2$-phen)]=(diaqua)(4,7-dimethyl-1,10-phenanthroline)oxovanadium (IV) sulfate;

[VO(Me$_2$-phen)$_2$]=(aqua)bis(4,7-dimethyl-1,10-phenanthroline)oxovanadium (IV) sulfate;

[VO(Cl-phen)]=(diaqua)(5-chloro-1,10-phenanthroline)oxovanadium (IV) sulfate;

[VO(Cl-phen)$_2$]=(aqua)bis(5-chloro-1,10-phenanthroline)oxovanadium (IV) sulfate;

[VO(bipy)]=(diaqua)(2,2'-bipyridyl)oxovanadium (IV) sulfate;

[VO(bipy)$_2$]=(aqua)bis(2,2'-bipyridyl)oxovanadium (IV) sulfate;

[VO(Me$_2$-bipy)]=(diaqua)(4,4'-dimethyl-2,2'-bipyridyl)oxovanadium (IV) sulfate;

[VO(Me$_2$-bipy)$_2$]=(aqua)bis(4,4'-bipyridyl)oxovanadium (IV) sulfate;

[VO(Br,OH-acph)$_2$]=bis(5'-bromo-2'-hydroxyacetophenone)oxovanadium (IV).

Unless otherwise indicated, the following abbreviations are used throughout the remainder of the disclosure:

CP, cyclopentadienyl

Cp$^-$, cyclopentadienyl anion acac, acetonylacetonate

Bpy, 2,2' Bipyridine

Hfacac, hexafluoroacetylacetonate

Cat, catecholate

Dtc, diethyl dithio carbamate

Phen, phenanthroline

PH, N-phenyl benzohydroxamic acids

H, acetohydroxamic acid

OTf, trifluoromethane sulphonate

THF, tetrahydrofuran

DMSO, dimethyl sulfoxide

CH$_3$CN, acetonitrile

CH$_2$Cl$_2$, dichloromethane d-d, laportte spin forbidden transitions

LMCT, ligand to metal charge transfer transitions p-p*, intraligand charge transfer transitions The present invention concerns vanadium compounds, and the finding that such compounds have potent and selective anti-mitotic activity, and are particularly active and stable agents for use in the treatment or inhibition of proliferative type cellular disorders, for example, cancer, pathologic hyperplasia, etc.

The vanadium compounds of the invention are also useful for disrupting or inhibiting meiosis, where disruption of meiosis is desired or useful.

Vanadium (IV) compounds for use in this invention are as shown in formula I and formula II

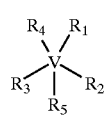

(I)

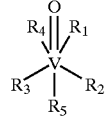

(II)

where $R_1$ and $R_2$ are each independently a monodentate ligand or together form a bidentate ligand; $R_3$ and $R_4$ are each independently a monodenate ligand or together form a bidentate ligand; and $R_5$ is a monodentate ligand, or is absent.

Suitable monodentate ligands include monodentate ligands are selected from the group consisting of halo, OH$_2$, O$_3$SCF$_3$, N$_3$, CN, OCn, SCn, SeCN, and a cyclpentadienyl ring, wherein each cyclopentadienyl ring is optionally substituted with one or more (C$_1$–C$_3$)alkyl. Suitable bidentate ligands are selected from the group consisting of acac, Bpy, Hfacac, Cat, Dtc, PH, H, and Phen, or derivatives thereof. The bidentate ligands may be substituted, for example, with one or more (C$_1$–C$_3$) alkyl, halo, (C$_1$–C$_3$) alkoxy, and halo (C$_1$–C$_3$) alkyl, and derivatives thereof. Halo is chloro, bromo, or iodo, and preferably is chloro.

In one embodiment, a useful vanadium compound has the following structure:

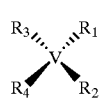

(III)

where $R_1$ and $R_2$ are each independently a monodentate ligand or together from a bidentate ligand; and $R_3$ and $R_4$ are each independently a cyclopentadienyl ring, wherein each cyclopentadienyl ring is optionally substituted with one or more (C$_1$–C$_3$)alkyl. In some preferred embodiments, $R_1$ and $R_2$ are each independently a monodentate ligand selected from the group consisting of of halo, OH$_2$, O$_3$SCF$_3$, N$_3$, CN, OCN, SCN, SeCN, and a cyclopentadienyl ring, where each cyclopentadienyl ring is optionally substituted with one or more (C$_1$–C$_3$)alkyl. Preferably, $R_1$ and $R_2$ arehalo, and more preferably are chloro.

In some other embodiments, $R_1$ and $R_2$ together form a bidentate ligand selected from the group consisting of acac, Bpy, Hfacac, Cat, Dtc, PH, H, and Phen, or derivatives thereof. Preferably, the bidentate ligand is acac, or derivatives thereof.

Some specific examples of compounds of formula I are: VC$_{p2}$Cl$_2$ (VDC), VD$_{p2}$Br$_2$, VC$_{p2}$I$_2$, VC$_{p2}$(N$_3$)$_2$, VC$_{p2}$(CN)$_2$, VC$_{p2}$(NCO)$_2$, VC$_{p2}$(NCO)Cl, VC$_{p2}$(NCS)$_2$, VC$_{p2}$(NCSe)$_2$, VC$_{p2}$Cl(CH$_3$CN)(FeCl$_4$), VC$_{p2}$(O$_3$SCF$_3$)$_2$, V(MeCp)$_2$Cl$_2$, V(Me$_5$Cp)$_2$Cl$_2$, VC$_{p2}$(acac) (VDacac), VC$_{p2}$(hf-acac), VC$_{p2}$(bpy), VC$_{p2}$(cat), VC$_{p2}$(dtc), VC$_{p2}$PH, or VC$_{p2}$H. Two particularly useful vandocene compounds are VDC and VDacac.

Useful oxovanadium compounds of formula II include the compound has the following structure:

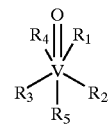

where $R_1$ and $R_2$ are each independently a monodentate ligand or together form a bidentate ligand; $R_3$ and $R_4$ together form a bidentate ligand; and $R_5$ is a monodentate ligand, or is absent. Preferably, $R_1$ and $R_2$ are each independently a monodentate ligand selected from the group consisting of halo, $OH_2$, $O_3SCF_3$, $N_3$, CN, OCN, SCN, SeCN, and a cyclopentadienyl ring, wherein each cyclopentadienyl ring is optionally substituted with one or more $(C_1-C_3)$alkyl, and $R_3$ and $R_4$ together form a bidentate ligand selected from the group consisting of acac, Bpy, Hfacac, Cat, Dtc, PH, H, and Phen, or derivatives thereof. Where $R_1$ and $R_2$ together form a bidentate ligand, the bidentate ligand is selected from the group consisting of acac, Bpy, Hfacac, Cat, Dtc, PH, H, and Phen, or a derivative thereof.

Specific compounds of formula II include [VO(phen)], [VO(phen)$_2$], [VO(Me$_2$-phen)], [VO(Me$_2$-phen($_2$], [VO(Cl-phen)], [VO(Cl-phen)$_2$], [VO(bipy)], [VO(bipy)$_2$], [VO(Me$_2$-bipy)], [VO(Me$_2$-bipy)$_2$], and [VO(Br,OH-acph)$_2$].

Compositions comprising these vanadium compounds are useful in the treatment of numerous proliferative cellular disorders, in particular disorders that involve invasion and migration of cells into surrounding tissue. Administration of the compounds as salts may be appropriate. Examples of acceptable salts include alkali metal (for example, sodium, potassium or lithium) or alkaline earth metal (for example calcium) salts, however, any salt that is non-toxic and effective when administered to the animal treated is acceptable. Acceptable salts may be obtained using standard procedures well known in the art, for example by reacting a sufficiently acidic compound with a suitable base affording a physiologically acceptable anion.

The compositions of the invention can be formulated as pharmaceutical compositions and administered to an animal host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. When administered orally, the compositions of the invention can preferably be administered in a gelatin capsule.

The tables, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or frustose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compositions of the invention may also be administered intravenously or intraperitoneally by infusion or injection. Solutions of the active composition can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active composition in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compositions may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin as known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compositions of the invention in a liquid composition, such as a lotion, will be from about 0.1–50 wt-%, preferably from about 0.5–5 wt %. The concentration in a semi-solid or solid composition such as a gel or a powder will be about 0.1–5 wt-%, preferably about 0.5–2.5 wt-%.

The amount of the composition required for use in treatment will vary not only with the particular salt selected but also with the route of administration, the nature of the condition being treated, and the age and condition of the patient, and will ultimately be at the discretion of the attendant physician or clinician.

In general, however, a suitable dose will be in the range of from about 0.1 to about 150 mg/kg, e.g., from about 10 to about 75 mg/kg of body weight per day, such as 3 to about 50 mg per kilogram body weight of the recipient per day, preferably in the range of 1 to 100 mg/kg/day, most preferably in the range of 5 to 20 mg/kg/day.

The compositions are conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of form about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the active ingredient, optionally in saline, or orally administered as a bolus containing about 1–1000 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Following i.m. administration, the compositions of the invention enter the blood stream within about 10–15 minutes and reach a maximum concentration in the blood within one hour of administration, at which point they can be found throughout the circulatory related organs.

In the method invention, vanadium compounds as described above, are useful as pharmaceutical compositions, administered to a subject to prevent metastatic cell adhesion, migration, and invasion into surrounding tissues.

EXAMPLES

The present invention may be better understood with reference to the accompanying examples that are intended for purposes of illustration only and should not be construed to limit the scope of the invention, as defined by the claims appended hereto.

Example 1

Synthesis of Vanadium Compounds

Compounds useful in the invention are prepared by known methods, as described, for example, in published PCT Applications WO99/36063; WO 00/27389; and WO 00/35930. For example, the oxovanadium (IV) complexes were synthesized based on previously published chemistry of VO(phen) and VO(phen)$_2$ complexes (Sakurai, et al., *Biochemical and Biophysical Research Communications,*. 206, No. 1, 1995; Selbin, et al., *Chemical Reviews,* 65, No. 2, 1965). Briefly, these complexes were synthesized by reacting an aqueous solution of vanadyl sulfate with an ethanol solution or a chloroform solution of the ligands.

The complexes purified from chloroform, ether and/or water were characterized by Fourier transform infrared spectroscopy (FT-Nicolet model Protege 460; Nicolet Instrument Corp., Madison, Wis.), US-visible spectroscopy (DU 7400 spectrophotometer; Beckman Instruments, Fullerton, Calif.) and element analysis (Atlantic Microlab, Inc., Norcross, Ga.). The se oxovanadium complexes have an octahedral or square pyramidal geometry with the oxo ligand (O$^2$) in the axial site. The oxovanadium complexes are stabilized with bidentate ligands that form a 5-membered ring with the vanadium atom. Structural variations of the ligands included addition of bromo, chloro or methyl groups on the phenanthroline, bipyridyl or acetophenone rings.

Example 2

Induction of Apoptosis in Cancer Cells

This example illustrates that vanadium compounds such as the organometallic compound bis (4,7-dimethyl-1,10-phenantroline) sulfatooxovanadium (IV) [(VO(SO$_4$)(Me-Phen)$_2$] exhibit potent cytotoxic activity against cancer cells such as brain tumor and breast cancer cells, and that this cytotoxic activity is mediated through the induction of apoptosis in treated cells.

Cell Lines

Human brain tumor cells lines U87 MG (Cat.# HTB-14), U118 MG (Cat. # HTB-15), U138 (Cat # HTB-16), U373 MG (CAT. # HTB-17), and T98G (Cat. # CRL-1690) and breast cancer cell lines BT-20 (Cat # HTB-19), MDA-MB-231 (Cat # HTB-26), MDA-MB-361 (Cat # HTB-27), and MCF-7 (Cat # HTB-22) were obtained from American Type Culture Collection (ATCC, Rockville, Md.) and maintained as continuous cell lines in Dulbecco's modified Eagles's medium (U87, U118, U138, U373, T98 and BT-20) or Leibovitz's L-15 medium (MDA-MB-231 and MDA-MB-361). All media were supplemented with 10% fetal calf serum (FCS), 4 mM glutamine, 100 U/ml penicillin G and 100 mg/ml streptomycin sulfate. All tissue culture reagents were obtained from Life Technologies Inc. (GIBCO-BRL, Gaithersburg, Md.).

Cytotoxicity MTT Assay

The cytotoxicity of [VO(SO$_4$)(Me$_2$-Phen)$_2$] against human cancer cell lines was analyzed using the MTT (3-[4,5-dimethylthiazol-2-yl]-2,5-diphenyl tetrazolium bromide) assay (Boehringer Mannheim Corp., Indianapolis, Ind.) as described previously (Narla et al., *Clin Cancer Res.*, 4: 1405–1414, 1998). Briefly, exponentially growing tumor cells were seeded into a 96-well plate at a density of 2.5×10$^4$ cells/well. [VO(SO$_4$)(Me$_2$-Phen)$_2$] was then added to each well to yield final concentrations ranging from 0.1 to 100 μM. Following incubation at 37° C. for 48 hours, 10 μl of MTT (0.5 mg/ml final concentration) was added to each well. The plates were then incubated at 37° C. for an additional 4 hours to allow MTT to form formazan crystals by reacting with metabolically active cells. The formazan crystals were solubilized overnight at 37° C. in a solution containing 10% SDS in 0.01M HCl. The absorbance at 540 nm (a reference wavelength of 690 nm was used) of the solution in each well was measured using a microplate reader (Labsystems). The percent survival and the IC$_{50}$ values were calculated using Graphpad Prism v2.0 (Graphpad Software, Inc., San Diego, Calif.) as described previously (Narla et al., Supra).

Human glioblastoma (U87, U118, U138, U373 and T98) and breast cancer cells (BT-20, MDA-MB-231, MDA-MB-361 and MCF-7) were incubated with increasing concentrations (0.1 μM to 100 μM) of [VO(SO$_4$)(Me$_2$-Phen)$_2$] for 48 h in 96-well plates. Cell survival was determined by MTT assays. The data points represent the mean (±SE) values from 3 independent experiments.

In situ Detection of Apoptosis

Apoptosis was detected using an in situ cell death detection kit (Boehringer Mannheim Corp., Indianapolis, Ind.) as described previously (Albini et al., *J. Cell Biol.*, 105: 1867–1872, 1987; Huang et al., *J Biol Chem.*, 272: 2927–2935, 1997). Cells were incubated with [VO(SO$_4$)(Me$_2$-Phen)$_2$] for 48 hours at 37° C., fixed, permeabilized, incubated with the reaction mixture containing terminal deoxynucleotidyl transferase (TdT) and fluorescein isothiocyanate (FITC)-conjugated dUTP and counterstained with propidium iodide. Cells were transferred to slides and viewed with confocal laser scanning microscope (Bio-Rad MRC 1024) mounted on a Nikon Eclipse E800 series upright microscope as previously reported (Narla et al., Supra).

Results

As shown in the table below, [VO(SO$_4$)(Me$_2$-Phen)$_2$] exhibited potent cytotoxic effects against five brain tumor and four breast cancer cell lines. Data from MTT assays demonstrated potent cytoxic activity of [VO(SO$_4$)(Me$_2$-Phen)$_2$] against each of the brain tumor and breast cancer cell lines with nanomolar or low micromolar IC$_{50}$ values.

| CELL TYPE | IC$_{50}$ (mean ± SE) |
|---|---|
| U87 | 2.1 ± 0.6 μM |
| U118 | 0.82 ± 0.1 μM |
| U138 | 2.7 ± 0.4 μM |
| U373 | 2.0 ± 0.4 μM |
| T98 | 3.9 ± 0.5 μM |
| BT-20 | 1.6 ± 0.7 μM |
| MDA-MB-231 | 0.5 ± 0.1 μM |
| MDA-MB-361 | 1.9 ± 0.5 μM |
| MCF-7 | 2.3 ± 0.4 μM |

Administration of [VO(SO$_4$)(Me$_2$-Phen)$_2$] to cells induced apoptotic or programmed cell death as determined using the TdT-mediated dUTP nick-end labeling of exposed 3'-OH termini of DNA with dUTP-FITC. Exemplary confocal laser scanning microscopy images were prepared, [VO(SO$_4$)(Me$_2$-phen)$_2$]-treated U87 glioblastoma and MDA-MB-231 breast cancer cells, examined for dUTP-FITC incorporation (green fluorescence) and propidium iodide counterstaining (red fluorescence), exhibited many apoptotic yellow nucleic (superimposed green and red fluorescence) at 24 hours after treatment. The apoptotic EC$_{50}$ values were 4.2±0.9 μM for the U87 cells and 2.1±0.4 μM for the MDA-MB-231 cells.

The data illustrates that compounds of the present invention are cytotoxic to tumor cells. The data also illustrates that the cytotoxic effects of the compounds are mediated through apoptosis. As such, the compounds of the present invention are useful in the treatment of hyperproliferative cellular disorders, for example, in cancer or hyperplasia.

Example 3

Impaired Tumor Cell Adhesion To Extracellular Matrix

This example illustrates that vanadium compounds of the invention, for example, the organometallic compound [(VO(SO$_4$)(Me-Phen)$_2$] impair the interaction between tumor cells and the extracellular matrix (ECM).

Adhesion Assays

In vitro adhesion assays were used to evaluate the effects of [VO(SO$_4$)(Me$_2$-Phen)$_2$] on the adhesive properties of U87 and MDA-MD-231 cells as described previously (Narla et al., *Clin Cancer Res*, 4: 2463–2471, 1998). The plates for the adhesion assays were pre-coated with the extracellular matrix (ECM) proteins laminin, fibronectin, vitronectin and type IV collagen (each at a final concentration of 1 μg/ml in PBS) overnight at 4° C. and dried. Exponentially-growing cells (as described in the previous Example) were incubated with [VO(SO$_4$)(Me$_2$-Phen)$_2$] at concentrations ranging from 0.5 μM to 25 μM for 16 hours in a humidified 5% CO$_2$ atmosphere. The cells were then detached from the flasks with 0.05% trypsin (Life Technologies), resuspended in medium, incubated at 37° C. for 2 hours to allow them to recover from the trypsinization stress and examined for their ability to adhere to the plates precoated with ECM proteins. Cells were centrifuged, washed twice with serum-free medium, counted and resuspended in serum-free medium at a final concentration of 2.5×10$^5$ cells/ml. The cell suspension was added to each well in aliquots of 100 μl and the cells were allowed to adhere for one hour at 37° C. in a humidified 5% CO$_2$ atmosphere. The non-adherent cells were removed by gently washing the cells with PBS. The adherent fraction was quantitated using MTT assays as previously described (Narla, Supra).

Results

U87 glioblastoma and MDA-MD-231 breast cancer cells were preincubated with various concentrations of [VO(SO$_4$)(Me$_2$-Phen)$_2$] and processed for adhesion assays. [VO(SO$_4$)(Me$_2$-Phen)$_2$] inhibited adhesion of the U87 and MDA-MB-231 cells to extracellular matrix (ECM) proteins, Pretreatment of cells with [VO(SO$_4$)(Me$_2$-Phen)$_2$] inhibited the adhesion of U87 glioblastoma and MDA-MB-231 breast cancer cells to laminin-, fibronectin-, vitronectin- and collagen-coated plates. The inhibition of glioblastoma cell adhesion was concentration-dependent with mean (±SE) IC$_{50}$ values from 3 independent experiments shown in the table below.

|            | laminin        | fibronectin    | vitronectin    | collagen       |
|------------|----------------|----------------|----------------|----------------|
| U87        | 1.4 ± 0.1 μM   | 1.3 ± 0.1 μM   | 1.2 ± 0.1 μM   | 1.2 ± 0.2 μM   |
| MDA-MB-231 | 1.0 ± 0.1 μM   | 1.0 ± 0.0 μM   | 1.1 ± 0.1 μM   | 1.3 ± 0.1 μM   |

The data illustrates that the compounds of the present invention are successful at impairing adhesion between tumor cells and the ECM. It is well known that adhesion to ECM proteins plays an important role in tumor cell attachment and migration (Carbonetto et al., *J Physiol*, 82: 258–270, 1987; Carbonetto et al., *Curr Open Neurobiol*, 1: 407–413, 1991; Giese et al., *Neurosurgery*, 38: 755–764, 1996; Giese et at., *Neurosurgery*, 37: 294–302, 1995; Merzak et al., *Cell Adhes Commun*, 3: 27–43, 1995; Rooprai et al., *Int J Dev Neurosci.*, 17: 613–623, 1999; Rutka et al., *J Neurosurg*, 69: 155–70, 1988; Venstrom et al., *Faseb J*, 7: 996–1003, 1993). As such, the data indicates that the compounds of the invention are useful in the treatment of invasive hyperproliferative cellular disorders, for example, in squamous cell carcinoma.

Example 4

[VO(SO$_4$)(Me$_2$-Phen)$_2$] Impairs Tumor Cell Migration

This example illustrates that the organometallic compound [(VO(SO$_4$)(Me-Phen)$_2$] impairs the migration and infiltration of tumor cells into surrounding tissue.

Migration Assay

Dissociation and migration are the initial steps for infiltration of tumor cells into the surrounding tissue (Pilkington et al., *Anticancer Res.*, 17: 4107–4109, 1997; Giese et al., *Neurosurgery*, 39: 235–252, 1996; Chintala et al., *Front Biosci*, 1: d324–39, 1996). Migration of brain tumor cells was monitored using U373 glioblastoma cell spheroids, as described previously (Narla et al., *Clin Cancer Res*, 4:2463–2471, 1998). Glioblastoma cell spheroids were cultured in 100 mm$^2$ tissue culture plates precoated with 0.75% agar prepared in MEM supplemented with 10% fetal bovine serum. The cells (5×10$^6$ cells) were suspended in the medium, seeded onto agar-coated plates and cultured for 5–7 days at 37° C. Spheroids with a diameter of 200–400 μm were selected for use in further experiments. For the migration experiments, the selected spheroids were incubated for 2 hours at 37° C. in serum-free medium containing [VO(SO$_4$)(Me$_2$-Phen)$_2$] in concentrations ranging from 1 μM to 25 μM. The [VO(SO$_4$)(Me$_2$-Phen)$_2$]-treated and vehicle control (DMSO, 0.1%) spheroids were transferred onto fibronectin-coated coverslips (Becton Dickinson, Bedford, Mass.) and placed in 6-well plates containing the same concentrations of [VO(SO$_4$)(Me$_2$-Phen)$_2$] or DMSO in serum-free medium. Spheroids were then kept in a humidified 5CO$_2$ incubator at 37° C. for 48 hours. A total of 4–6 spheroids were used for each concentration. Following the 48 hours incubation period, the spheroids were fixed and stained with Hema-3 solutions and mounted onto glass slides. The distance of tumor cell migration from the spheroid was measured using an ocular micrometer and a transmitted light microscope.

In vitro Invasion Assays

Tumor invasion of the basement membrane is a crucial step in the complex multistage process that leads to metastatic spread. Tumor cells cross the basement membrane as they initially invade the lymphatic or vascular beds during dissemination and as they penetrate their target tissues. (Nagano et al., *Acta Neuropathol*, 86: 117–125, 1993; Pilkington et al., *Braz J Med Biol Res*, 29: 1159–1172, 1996; Schiffer et al., *Acta Neuropathol*, 77: 369–378, 1989; Brown et al., *Clin Cancer Res*, 5: 1041–1056, 1999). the Matrigel matrix, an artificial basement membrane composed of growth factors and several ECM components such as collagens, laminin and proteoglycans, was used to examine tumor cell invasion after administration of the vanadium compound, [VO(SO$_4$)Me$_2$-Phen)$_2$].

Invasion of cancer cells treated with [VO(SO$_4$)(Me$_2$-Phen)$_2$] was assayed using Matrigel-coated Costar 24-well transwell cell culture chambers ("Boyden chambers") with 8.0-μm-pore polycarbonate filter inserts as described previously (Narla et al., *Clin Cancer Res*, 4: 2463–2471, 1998; Ghosh et al., *Anticancer Drug Des*, 14: 403–410, 1999; Albini et al., *J Cell Biol*, 105: 1867–1872, 1987). Exponentially-growing U87 and MDA-MB-231 cells were incubated with [VO(SO$_4$)(Me$_2$-Phen)$_2$] at various concentrations ranging from 0.5 μM to 25 μM overnight. The cells were trypsinized, washed twice with serum-free medium containing BSA, counted and resuspended in a serum-free medium at 1×10$^5$ cells/ml. The cell suspension (0.5 mL aliquots) was added to the Matrigel-coated and rehydrated filter inserts. The inserts were then placed in 24-well plates containing 750 μl of NIH fibroblast-conditioned medium as a chemoattractant, and incubated at 37° C. for 48 hours. The filter inserts were then removed, the medium was decanted and the cells on the top of the filter that did not migrate were scraped off with a cotton-tipped applicator. The invasive cells that migrated to the lower side of the filter were fixed, stained with Hema-3 solution and counted under a light microscope. Five to 10 random fields per filter were counted to determine the invasive fraction. The invasive fractions of cells treated with [VO(SO$_4$)(Me$_2$-Phen)$_2$] were compared to those of DMSO-treated control cells and the percent inhibition of invasiveness was determined.

Results

Spheroids measuring 259.2±41.9 μm in diameter were incubated with [VO(SO$_4$)(Me$_2$-Phen)$_2$] or DMSO on fibronectin-coated coverslips. The U373 gioblastoma cells incubated with DMSO rapidly migrated to a distance 745±29 μm away from the spheroid. Treatment of the spheroids with [VO(SO$_4$)(Me$_2$-Phen)$_2$], however, inhibited tumor cell migration in a concentration-dependent fashion with an IC$_{50}$ value of 1.4±0.2 μM. Treatment with 1 μM and 2 μM [VO(SO$_4$)(Me$_2$-Phen)$_2$] resulted in 58.3±7.3% (migration distance of 311.1±54.4 μm) and 71.2±3.4% (migration distance of 214.9±25.7 μm) inhibition of tumor cell migration from the spheroids, respectively.

To determine if [VO(SO$_4$)(Me$_2$-Phen)$_2$] impairs cancer cell invasion through Matrigel, cancer cells were incubated with various concentrations of the compound. Invasion of treated MDA-MB-231 and U87 cells was examined. Cells were incubated for 24 hours with [VO(SO$_4$)(Me$_2$-Phen)$_2$] in concentrations ranging from 0.5 μM to 10 μM. The cells were then trypsinized and processed for invasion assays using Matrigel matrix-coated Boyden chambers. The data points represent the mean (±SE) values from 3 independent experiments.

The data showed that administration of the vanadium compound to cancer cells inhibited their invasion through Matrigel matrix as compared with non-treated controls in a concentration-dependent fashion. Mean IC$_{50}$ values were 0.78±0.4 µM for U87 cells and 0.6±0.3 µM for MDA-MD-231 cells. The data illustrates that the compounds of the present invention are successful at impairing both tumor cell invasion and migration and, as such, are useful compounds in the inhibition of metastatic disease.

Example 5

In Vivo Inhibition of Metastatic Cancer

This example illustrates the vanadium compounds of the invention, and specifically the organometallic compound [(VO(SO$_4$)(Me-Phen)$_2$] are effective to prevent and/or inhibit metastatic cancer, in vivo. The activity was tested SCID/nude mouse xenograft models. The data indicates that [(VO(SO$_4$)(Me-Phen)$_2$], and other oxovanadium compounds, have utility as compounds in the treatment of cancer and especially in the case of metastatic cancer.

Maintenance of SCID and Nude Mouse Colony

The animal protocols used in this study were approved by the Parker Hughes Institute Institutional Animal Care and Use Committee (IACUC). Female CB.17 severe combined immuno-deficient (SCID) and NCr nude mice were obtained from Taconic (Germantown, N.Y.) and housed in a specific pathogen-free room located in a secure indoor facility with controlled temperature, humidity, and noise levels. Mice were housed in microisolater cages and fed with autoclaved rodent chow. Water was also autoclaved and supplemented with trimethoprim/sulfomethoxazol 3 days/week.

SCID Mouse Xenograft Model of Human Glioblastoma and Breast Cancer

The right and left hind legs of the SCID mice were inoculated subcutaneously with 1×10$^6$ U87 human glioblastoma and 1×10$^6$ MDA-MB-231 beast cancer cells, respectively, in 0.1 mL PBS. The mice challenged with tumor cells were treated with intraperitoneally-administered injections of [VO(SO$_4$)(Me$_2$-Phen)$_2$] (10 mg/kg in 5% DMSO in PBS; n=10) or vehicle alone (5% DMSO in PBS; n=10). Injections were given once daily, five days per week, for four consecutive weeks beginning the day after inoculation of the tumor cells. Mice were monitored daily for health status as well as tumor growth and were sacrificed if they became moribund, developed tumors which impeded their ability to attain food or water, or at the ed of the six-week observation period. Tumors were measured using Vernier calipers three times per week. Tumor volumes were calculated according to the following formula, as described previously (Narla et al., *Clin Cancer Res.*, 4: 1405–14, 1998; Friedman et al., Cancer Res., 55: 2853–2857, 1995): Tumor volume=(Width)$^2$(Length)/2. For histopathologic studies, tissues were fixed in 10% neutral buffered formalin, dehydrated, and embedded in paraffin by routine methods. Glass slides with affixed 6 µm tissue sections were prepared and stained with hematoxylin/eosin.

Nude Mouse Model of Intracranial Glioblastoma

Nude mice were anesthetized with Avertin (2,2,2-tribromoethanol in tert-amyl alcohol; Aldrich Chemical Co., Milwaukee, Wis.) at a dose of 0.5 mg/g under aseptic conditions in a laminar flow hood. A small hole was drilled through the skull 2 mm to the right of the midline and 2 mm posterior to the bregma. U87 glioblastoma cells (4×10$^5$ cells in 10 µl of PBS) were intracranially implanted into the right side of the cerebral hemisphere of the mice using a Hamilton syringe fitted to a stereotaxic apparatus with a mouse adaptor (David Kopf Instruments, Tujunga, Calif.) as described earlier (34). Twenty-four hours after inoculation, mice were treated intraperitoneally with [VO(SO$_4$)(Me$_2$-Phen)$_2$] (10 mg/kg/day, n=10) or vehicle (5% DMSO in PBS, n=11) for ten consecutive days. Seventeen days after incobuation, two mice from each group were sacrificed. The grains were then fixed in formalin, processed for histopathology and the tumor volumes from histological sections were measured as described earlier (Haung et al., *J. Biol Chem*, 272; 2927–2935, 1997). the remaining mice were monitored twice a day for survival.

Results

Following intracranial implantation of 4×10$^5$ U87 glioblastoma cells (in 10 µl of PBS) into the right cerebral hemispheres of NCr number mice [VO(SO$_4$)(Me$_2$-Phen)$_2$] (10 mg/kg/day; n=10) or vehicle (5% DMSO in PBS; n=11) was administered peritoneally daily for ten days. The mice wee monitored twice a day for health status. CB.17 SCID mice developed rapidly growing tumors after subcutaneous inoculation of 1×10$^6$ U87 glioblastoma or MDA-MB-231 breast cancer cells.

Figure 2:
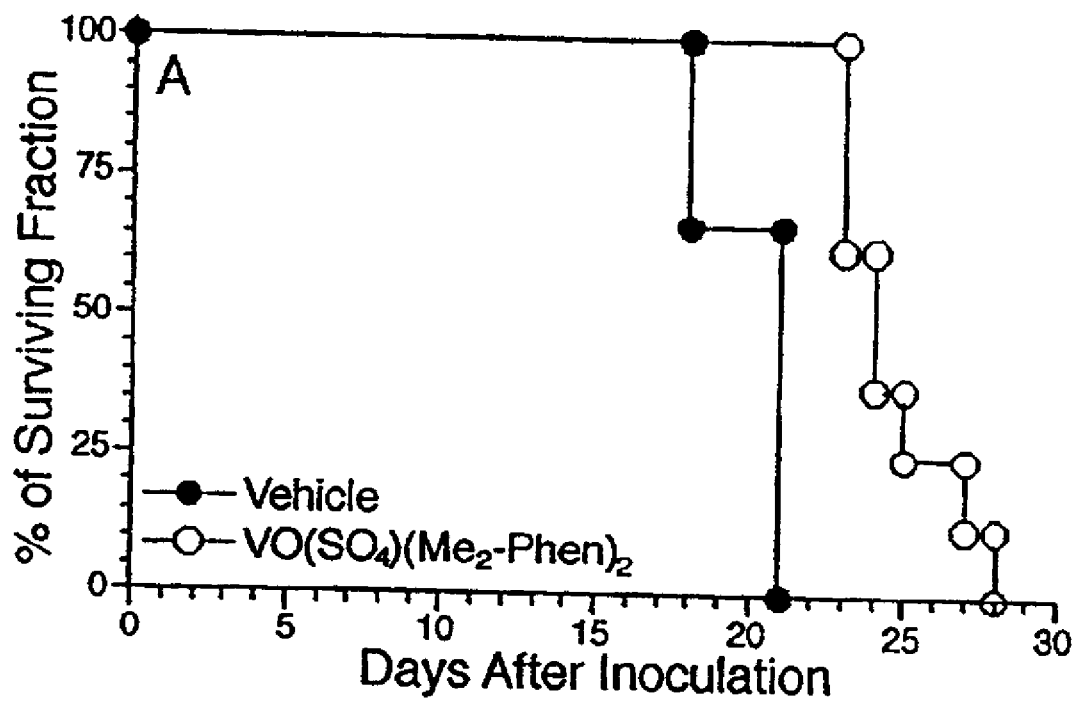
FIG. 2 illustrates the in vivo antitumor activity of [VO(SO$_4$)(Me$_2$-Phen)$_2$] against intracranial U87 glioblastoma in nude mice. A representative survival curve of [VO(SO$_4$)(Me$_2$-Phen)$_2$]-treated (n=8) and control (n=9) mice is shown.

[VO(SO$_4$)(Me$_2$-Phen)$_2$] significantly delayed the onset of tumor growth and inhibited visible tumor progression when administered intraperitoneally in single daily injections (10 mg/kg/dose) given five days per week for four weeks beginning the day after subcutaneous inoculation of the tumor cells (FIG. 2). All of the control mice developed measurable tumors within 7 days, whereas 40% of the mice with U87 xenographs treated with [VO(SO$_4$)(Me$_2$-Phen)$_2$] remained alive and free of detectable tumors for >16 days. At 1.5 months after the inoculation of tumor cells, the average size of the U87 tumor xenografts in vehicle-treated control SCID mice was 6928±653 mm$^3$, whereas the average size of the U87 tumors in [VO(SO$_4$)(Me$_2$-Phen)$_2$]-treated SCID mice was only 3199±646 mm$^3$ (P=0.007) (FIG. 1A). Similarly, the average size of MDA-MB-231 tumors in vehicle-treated control SCID mice at 1.5 months after tumor cell inoculation was 641±98.7 mm$^3$, while the average size of MDA-MD-231 tumors in [VO(SO$_4$)(Me$_2$-Phen)$_2$]-treated SCID mice was 286.9±41.5 mm$^3$ (P=0.004) (FIG. 1B). Ninety percent of the control mice developed measurable tumors within 7 days, whereas 50% of the mice treated with [VO(SO$_4$)(Me$_2$-Phen)$_2$] remained alive and free of detectable tumors for >19 days.

NCr nude mice implanted with U87 glioblastoma cells intracranially rapidly developed tumors with a median survival time of 19.6±0.6 days. As shown in FIG. 2, [VO(SO$_4$)(Me$_2$-Phen)$_2$] administered peritoneally (10 mg/kg/day) for ten consecutive days significantly improved the survival time of the mice (median survival time: 24.4±0.8 days; P=0.0002). All of the vehicle-treated mice died within 21 days of intracranial tumor cell implantation, while over 60% of [VO(SO$_4$)(Me$_2$-Phen)$_2$]-treated mice remained alive for >24 days. The average tumor volume 17 days after tumor cell inoculation was approximately 2.9-fold less for the [VO(SO$_4$)(Me$_2$-Phen)$_2$]-treated mice than for the vehicle-treated control mice.

The data illustrates that compounds of the present invention exhibit significant in vivo activity effective to prevent and/or inhibit tumor development in a SCID/nude mouse xenograft model of human metastatic glioblastoma and breast cancer.

The above specification, examples and data provide a complete description of the manufacture and use of the composition of the invention. Since many embodiments of the invention can be made without departing from the spirit and scope of the invention, the invention resides in the claims hereinafter appended.

The specification recites numerous patents and publications, each which is expressly incorporated by reference as if fully set forth.

We claim:
1. A method for inhibiting adhesion, migration, or invasion of a non-cancer proliferative cell, comprising administering to the cell a vanadium compound having the following structure:

(II)

wherein,
$R_1$ and $R_2$ are each independently a monodentate ligand or together form a bidentate ligand;
$R_3$ and $R_4$ are each independently a monodentate ligand or together form a bidentate ligand; and
$R_5$ is a monodentate ligand, or is absent;
wherein
each monodentate ligand is halo, $OH_2$, $O_3SCF_3$, $N_3$, CN, OCN, SCN, SeCN, or a cyclopentadienyl ring that can be substituted with one or more $(C_1-C_3)$alkyl; and
each bidentate ligand is acetonylacetonate, 2,2'-bipyridine, hexafluoroacetylacetonate, diethyl dithiocarbamate, N-phenyl benzohydroxamic acid, acethydroxamic acid, phenanthroline, or a derivative thereof.

2. The method of claim 1, wherein $R_1$ and $R_2$ together form a bidentate ligand.

3. The method of claim 2, wherein the bidentate ligand is 2,2'-bipyridine, phenanthroline, or a derivative thereof.

4. The method of claim 2, wherein the bidentate ligand is optionally substituted with one or more of halo, $(C_1-C_3)$ alkyl, $(C_1-C_3)$ alkoxy, or halo $(C_1-C_3)$ alkyl.

5. The method of claim 2, wherein the bidentate ligand is phenanthroline optionally substituted with one or more of halo, $(C_1-C_3)$ alkyl, $(C_1-C_3)$ alkoxy, or halo $(C_1-C_3)$ alkyl.

6. The method of claim 2, wherein the bidentate ligand is 1,10-phenanthroline; 4,7-dimethyl-1,10-phenanthroline; 5-chloro-1,10-phenanthroline; 5'-bromo-2'-hydroxyacetophenone; 2,2'-bipyridine; or 4,4'-dimethyl-2,2'bipyridine.

7. The method of claim 2, wherein the bidentate ligand is 4,7-dimethyl-1,10-phenanthroline.

8. The method of claim 2, wherein $R_3$ and $R_4$ together form a bidentate ligand.

9. The method of claim 8, wherein the bidentate ligands formed by $R_1$ and $R_2$ and by $R_3$ and $R_4$ are phenanthroline optionally substituted with one or more of halo, $(C_1-C_3)$ alkyl, $(C_1-C_3)$ alkoxy, or halo $(C_1-C_3)$alkyl.

10. The method of claim 8, wherein the bidentate ligands formed by $R_1$ and $R_2$ and by $R_3$ and $R_4$ are 1,10-phenanthroline; 4,7-dimethyl-1,10-phenanthroline; 5-chloro-1,10-phenanthroline; 5'-bromo-2'-hydroxyacetophenone; 2,2'-bipyridine; or 4,4'-dimethyl-2,2'bipyridine.

11. The method of claim 8, wherein the bidentate ligands formed by $R_1$ and $R_2$ and by $R_3$ and $R_4$ are 4,7-dimethyl-1,10-phenanthroline.

12. The method of claim 1, wherein the vanadium compound is: (diaqua)(1,10-phenanthroline)oxovanadium (IV) sulfata, (aqua)bis(1,10-phenanthroline)oxovanadium (IV) sulfate, (diaqua)(4,7-dimethyl-1,10-phenanthroline) oxovanadium (IV) sulfate, (aqua)bis(4,7-dimethyl-1,10-phenanthroline)oxovanadium (IV) sulfate, (diaqua)(5-chloro-1,10-phenanthroline)oxovanadium (IV) sulfate, or (aqua) bis(5-chloro-1,10-phenanthroline)oxovanadium (IV) sulfate.

13. The method of claim 1, wherein the vanadium compound is (diaqua)(2,2'bipyridyl)oxovanadium (IV) sulfate, (aqua)bis(2,2'-bipyridyl)oxovanadium (IV) sulfate, (diaque) (4,4'-dimethyl-2,2'-bipyridyl) oxovanadium (IV) sulfate, (aqua)bis(4,4'-dimethyl-2,2'-bipyridyl)oxovanadium (IV) sulfate or bis(5'-bromo-2'-hydroxyacetophenone) oxovanadium (IV).

14. The method of claim 1, wherein said vanadium compound is (aqua)bis(4,7-dimethyl-1,10-phenanthroline) oxovanadium (IV) sulfate.

15. The method of claim of 1 wherein a plurality of non-cancer proliferative cells comprise independently hyperplasia, polyeythemia, erythrocythermia, thrombocythemia, EBV transformed lymphoproliferative syndrome, dysplastic nevus syndrome, restenosis, mastocytosis, histocytosis, psoriasis, or polyps.

16. The method of claim 15 wherein hyperplasia is epithelial hyperplasia.

17. The method of claim 15 wherein restenosis is restenosis after angioplasty.

18. A method for treating a non-cancer proliferative disorder in a subject, comprising administering to the subject a vanadium compound having the following structure:

(II)

wherein
$R_1$ and $R_2$ are each independently a monodentate ligand or together form a bidentate ligand;
$R_3$ and $R_4$ are each independently a monodentate ligand or together form a bidentate ligand; and
$R_5$ is a monodentate ligand, or is absent;
wherein
each monodentate ligand is halo, $OH_2$, $O_3SCF_3$, $N_3$, CN, OCN, SCN, SeCN, or a cyclopentadienyl ring that can be substituted with one or more $(C_1-C_3)$alkyl; and
each bidentate ligand is acetonylacetonate, 2,2'bipyridine, hexafluoroacetylacetonate, diethyl dithiocarbamate, N-phenyl benzohydroxamic acid, acethydroxamic acid, phenanthroline, or a derivative thereof.

19. The method of claim 18, wherein $R_1$ and $R_2$ together form a bidentate ligand.

20. The method of claim 19, wherein the bidentate ligand is 2,2'-bipyridine or phenanthroline, or a derivative thereof.

21. The method of claim 19, wherein the bidentate ligand is optionally substituted with one or more of halo, $(C_1-C_3)$ alkyl, $(C_1-C_3)$ alkoxy, or halo $(C_1-C_3)$ alkyl.

22. The method of claim 19, wherein the bidentate ligand is phenanthroline optionally substituted with one or more of halo, $(C_1-C_3)$ alkyl, $(C_1-C_3)$ alkoxy, or halo $(C_1-C_3)$ alkyl.

23. The method of claim 19, wherein the bidentate ligand is 1,10-phenanthroline; 4,7-dimethyl-1,10-phenanthroline; 5-chloro-1,10-phenanthroline; 5'-bromo-2'-hydroxyacetophenone; 2,2'-bipyridine; or 4,4'-dimethyl-2,2'bipyridine.

24. The method of claim 19, wherein the bidentate ligand is 4,7-dimethyl-1,10-phenanthroline.

25. The method of claim 19, wherein $R_3$ and $R_4$ together form a bidentate ligand.

26. The method of claim 25, wherein the bidentate ligands formed by $R_1$ and $R_2$ and by $R_3$ and $R_4$ are phenanthroline optionally substituted with one or more of halo, $(C_1-C_3)$ alkyl, $(C_1-C_3)$ alkoxy, or halo $(C_1-C_3)$ alkyl.

27. The method of claim 25, wherein the bidentate ligands formed by $R_1$ and $R_2$ and by $R_3$ and $R_4$ are 1,10-phenanthroline; 4,7-dimethyl-1,10-phenanthroline; 5-chloro-1,10-phenanthroline; 5'-bromo-2'-hydroxyacetophenone; 2,2'-bipyridine; or 4,4'-dimethyl-2,2'bipyridine.

28. The method of claim 25, wherein the bidentate ligands formed by $R_1$ and $R_2$ and by $R_3$ and $R_4$ are 4,7-dimethyl-1,10-phenanthroline.

29. The method of claim 18, wherein the vanadium compound is: (diaqua)(1,10-phenanthroline)oxovanadium (IV) sulfate, (aqua)bis(1,10-phenanthroline)oxovanadium (IV) sulfate, (diaqua)(4,7-dimethyl-1,10-phenanthroline) oxovanadium (IV) sulfate, (aqua)bis(4,7-dimethyl-1,10-phenanthroline)oxovanadium (IV) sulfate, (diaqua)(5-chloro-1,10-phenanthroline)oxovanadium (IV) sulfate, or (aqua)bis(5-chloro-1,10-phenanthroline)oxovanadium (IV) sulfate.

30. The method of claim 18, wherein the vanadium compound is (diaqua)(2,2'-bipyridyl)oxovanadium (IV) sulfate, (aqua)bis(2,2'-bipyridyl)oxovanadium (IV) sulfate, (diaqua)(4,4'-dimethyl-2,2'-bipyridyl)oxovanadium (IV) sulfate, (aqua)bis(4,4'-dimethyl-2,2'-bipyridyl) oxovanadium (IV) sulfate or bis(5'-bromo-2'-hydroxyacetophenone)oxovanadium(IV).

31. The method of claim 18, wherein said vanadium compound is (aqua)bis(4,7-dimethyl-1,10-phenanthroline) oxovanadium (IV) sulfate.

32. The method of claim of 18 wherein the non-cancer proliferative disorder is independently hyperplasia, polycythemia, erythrocythemia, thrombocythemia, EBV transformed lymphoproliferative syndrome, dysplastic nevus syndrome, restenosis, mastocytosis, histocytosis, psoriasis, or polyps.

33. The method of claim 32 wherein hyperplasia is epithelial hyperplasia.

34. The method of claim 32 wherein restenosis is restenosis after angioplasty.

* * * * *